(12) United States Patent
Desmet et al.

(10) Patent No.: US 10,280,442 B2
(45) Date of Patent: May 7, 2019

(54) MUTANT SUCROSE PHOSPHORYLASES WITH IMPROVED GLYCOSYLATION ACTIVITY TOWARDS POLYPHENOLS

(71) Applicant: Universiteit Gent, Ghent (BE)

(72) Inventors: Tom Desmet, Nevele (BE); Mareike Dirks-Hofmeister, Laudenbach (DE); Karel De Winter, Zottegem (BE); Tom Verhaeghe, Zwevegem (BE)

(73) Assignee: UNIVERSITEIT GENT, Ghent (BE)

( * ) Notice: Subject to any disclaimer, the term of this patent is extended or adjusted under 35 U.S.C. 154(b) by 0 days.

(21) Appl. No.: 15/571,602

(22) PCT Filed: May 10, 2016

(86) PCT No.: PCT/EP2016/060421
§ 371 (c)(1),
(2) Date: Nov. 3, 2017

(87) PCT Pub. No.: WO2016/180818
PCT Pub. Date: Nov. 17, 2016

(65) Prior Publication Data
US 2018/0142276 A1    May 24, 2018

(30) Foreign Application Priority Data
May 12, 2015  (EP) .................... 15167263

(51) Int. Cl.
| C12P 19/14 | (2006.01) |
| C12N 9/10 | (2006.01) |
| C12P 19/44 | (2006.01) |
| C07H 15/203 | (2006.01) |
| C07H 1/00 | (2006.01) |

(52) U.S. Cl.
CPC .............. *C12P 19/44* (2013.01); *C07H 1/00* (2013.01); *C07H 15/203* (2013.01); *C12N 9/1051* (2013.01); *C12Y 204/01007* (2013.01)

(58) Field of Classification Search
None
See application file for complete search history.

(56) References Cited

FOREIGN PATENT DOCUMENTS

WO    2014/060452    4/2014

OTHER PUBLICATIONS

Chica et al. Curr Opin Biotechnol. Aug. 2005;16(4):378-84. (Year: 2005).*
Singh et al. Curr Protein Pept Sci. 2017, 18, 1-11 (Year: 2017).*
Accession D9TT09. Oct. 5, 2010. (Year: 2010).*
International Search Report dated Jul. 19, 2016 in International (PCT) Application No. PCT/EP2016/060421.
Written Opinion of the International Searching Authority dated Jul. 19, 2016 in International (PCT) Application No. PCT/EP2016/060421.
Tom Verhaeghe, et al., "The Quest for a Thermostable Sucrose Phosphorylase Reveals Sucrose 6'-phosphate phosphorylase as a Novel Specificity", Applied Microbiology and Biotechnology, vol. 98, No. 16, 2014, pp. 7027-7037.
Mareike E. Dirks-Hofmeister, et al., "Creating Space for Large Acceptors: Rational Biocatalyst Design for Resveratrol Glycosylation in an Aqueous System", Angewandte Chemie International Edition, vol. 54, No. 32, 2015, pp. 9289-9292.
Dirk Aerts, et al., "Transglucosylation Potential of Six Sucrose Phosphorylases Toward Different Classes of Acceptors", Carbohydrate Research, vol. 346, 2011, pp. 1860-1867.
Karel De Winter, et al., "Biphasic Catalysis with Disaccharide Phosphorylases: Chemoenzymatic Synthesis of α-DGlucosides Using Sucrose Phosphorylase", Organic Process Research & Development, vol. 18, 2014, pp. 781-787.
Karel De Winter, et al., "Ionic Liquids as Cosolvents for Glycosylation by Sucrose Phosphorylase: Balancing Acceptor Solubility and Enzyme Stability", Green Chemistry, vol. 15, 2013, pp. 1949-1955.
Satoshi Kitao, et al., "The Syntheses of Catechin-glucosides by Transglycosylation with *Leuconostoc mesenteroides* Sucrose Phosphorylase", Bioscience, Biotechnology, and Biochemistry, vol. 57, No. 12, 1993, pp. 2010-2015.

* cited by examiner

*Primary Examiner* — Christian L Fronda
(74) *Attorney, Agent, or Firm* — Wenderoth, Lind & Ponack, L.L.P.

(57) ABSTRACT

The present invention relates to glycosylating polyphenols via biocatalysis. More specifically the present invention discloses particular mutants of the thermostable sucrose phosphorylase derived from the microorganism *Thermoanaerobacterium thermosaccharolyticum* which efficiently glycosylate polyphenols such as resveratrol.

8 Claims, 4 Drawing Sheets

Specification includes a Sequence Listing.

Fig. 2 bis

Fig. 3

SEQUENCE LISTING

<160> NUMBER OF SEQ ID NOS: 6

<210> SEQ ID NO 1
<211> LENGTH: 488
<212> TYPE: PRT
<213> ORGANISM: Artificial sequence
<220> FEATURE:
<223> OTHER INFORMATION: mutant of sucrose phosphorylase of bacterium
    Thermoanaerobacterium thermosaccharolyticum

<400> SEQUENCE: 1

```
Met Ala Leu Lys Asn Lys Val Gln Leu Ile Thr Tyr Pro Asp Ser Leu
1               5                   10                  15

Gly Gly Asn Leu Lys Thr Leu Asn Asp Val Leu Glu Lys Tyr Phe Ser
            20                  25                  30

Asp Val Phe Gly Gly Val His Ile Leu Pro Pro Phe Pro Ser Ser Gly
        35                  40                  45

Asp Arg Gly Phe Ala Pro Ile Thr Tyr Ser Glu Ile Glu Pro Lys Phe
    50                  55                  60

Gly Thr Trp Tyr Asp Ile Lys Lys Met Ala Glu Asn Phe Asp Ile Leu
65                  70                  75                  80

Leu Asp Leu Met Val Asn His Val Ser Arg Arg Ser Ile Tyr Phe Gln
                85                  90                  95

Asp Phe Leu Lys Lys Gly Arg Lys Ser Glu Tyr Ala Asp Met Phe Ile
            100                 105                 110

Thr Leu Asp Lys Leu Trp Lys Asp Gly Lys Pro Val Lys Gly Asp Ile
        115                 120                 125

Glu Lys Met Phe Leu Ala Arg Thr Leu Pro Tyr Ser Thr Phe Lys Ile
    130                 135                 140

Glu Glu Thr Gly Glu Glu Glu Lys Val Trp Thr Thr Phe Gly Lys Thr
145                 150                 155                 160

Asp Pro Ser Glu Gln Ile Asp Leu Asp Val Asn Ser His Leu Val Arg
                165                 170                 175

Glu Phe Leu Leu Glu Val Phe Lys Thr Phe Ser Asn Phe Gly Val Lys
            180                 185                 190

Ile Val Arg Leu Asp Ala Val Gly Tyr Val Ile Lys Lys Ile Gly Thr
```

```
            195                 200                 205
Ser Cys Phe Val Glu Pro Glu Ile Tyr Glu Phe Leu Asp Trp Ala
        210                 215                 220
Lys Gly Gln Ala Ala Ser Tyr Gly Ile Glu Leu Leu Leu Glu Val His
225                 230                 235                 240
Ser Gln Phe Glu Val Gln Tyr Lys Leu Ala Glu Arg Gly Phe Leu Ile
                245                 250                 255
Tyr Asp Phe Ile Leu Pro Phe Thr Val Leu Tyr Thr Leu Ile Asn Lys
                260                 265                 270
Ser Asn Glu Met Leu Tyr His Tyr Leu Lys Asn Arg Pro Ile Asn Gln
                275                 280                 285
Phe Thr Met Leu Asp Cys His Asp Gly Ile Pro Val Lys Pro Asp Leu
        290                 295                 300
Asp Gly Leu Ile Asp Thr Lys Lys Ala Lys Glu Val Val Asp Ile Cys
305                 310                 315                 320
Val Gln Arg Gly Ala Asn Leu Ser Leu Ile Tyr Gly Asp Lys Tyr Lys
                325                 330                 335
Ser Glu Asp Gly Phe Asp Val His Gln Ile Asn Cys Thr Tyr Tyr Ser
                340                 345                 350
Ala Leu Asn Cys Asp Asp Ala Tyr Leu Ala Ala Arg Ala Ile Gln
                355                 360                 365
Phe Phe Thr Pro Gly Ile Pro Gln Val Tyr Tyr Val Gly Leu Leu Ala
        370                 375                 380
Gly Val Asn Asp Phe Glu Ala Val Lys Lys Thr Lys Glu Gly Arg Glu
385                 390                 395                 400
Ile Asn Arg His Asn Tyr Gly Leu Lys Glu Ile Glu Ser Val Gln
                405                 410                 415
Lys Asn Val Val Gln Arg Leu Leu Lys Leu Ile Arg Phe Arg Asn Glu
                420                 425                 430
Tyr Glu Ala Phe Asn Gly Glu Phe Phe Ile Glu Asp Cys Arg Lys Asp
                435                 440                 445
Glu Ile Arg Leu Thr Trp Lys Lys Asp Asp Lys Arg Cys Ser Leu Phe
        450                 455                 460
Ile Asp Leu Lys Thr Tyr Lys Thr Thr Ile Asp Tyr Ile Asn Glu Asn
465                 470                 475                 480
Gly Glu Glu Val Lys Tyr Leu Val
                485

<210> SEQ ID NO 2
<211> LENGTH: 488
<212> TYPE: PRT
<213> ORGANISM: Artificial sequence
<220> FEATURE:
<223> OTHER INFORMATION: mutant of sucrose phosphorylase of bacterium
      Thermoanaerobacterium thermosaccharolyticum

<400> SEQUENCE: 2

Met Ala Leu Lys Asn Lys Val Gln Leu Ile Thr Tyr Pro Asp Ser Leu
1               5                   10                  15
Gly Gly Asn Leu Lys Thr Leu Asn Asp Val Leu Glu Lys Tyr Phe Ser
                20                  25                  30
Asp Val Phe Gly Gly Val His Ile Leu Pro Pro Phe Pro Ser Ser Gly
            35                  40                  45
Asp Arg Gly Phe Ala Pro Ile Thr Tyr Ser Glu Ile Glu Pro Lys Phe
        50                  55                  60
```

```
Gly Thr Trp Tyr Asp Ile Lys Lys Met Ala Glu Asn Phe Asp Ile Leu
 65                  70                  75                  80

Leu Asp Leu Met Val Asn His Val Ser Arg Arg Ser Ile Tyr Phe Gln
                 85                  90                  95

Asp Phe Leu Lys Lys Gly Arg Lys Ser Glu Tyr Ala Asp Met Phe Ile
            100                 105                 110

Thr Leu Asp Lys Leu Trp Lys Asp Gly Lys Pro Val Lys Gly Asp Ile
        115                 120                 125

Glu Lys Met Phe Leu Val Arg Thr Leu Pro Tyr Ser Thr Phe Lys Ile
    130                 135                 140

Glu Glu Thr Gly Glu Glu Lys Val Trp Thr Thr Phe Gly Lys Thr
145                 150                 155                 160

Asp Pro Ser Glu Gln Ile Asp Leu Asp Val Asn Ser His Leu Val Arg
                165                 170                 175

Glu Phe Leu Leu Glu Val Phe Lys Thr Phe Ser Asn Phe Gly Val Lys
            180                 185                 190

Ile Val Arg Leu Asp Ala Val Gly Tyr Val Ile Lys Lys Ile Gly Thr
        195                 200                 205

Ser Cys Phe Phe Val Glu Pro Glu Ile Tyr Glu Phe Leu Asp Trp Ala
    210                 215                 220

Lys Gly Gln Ala Ala Ser Tyr Gly Ile Glu Leu Leu Glu Val His
225                 230                 235                 240

Ser Gln Phe Glu Val Gln Tyr Lys Leu Ala Glu Arg Gly Phe Leu Ile
                245                 250                 255

Tyr Asp Phe Ile Leu Pro Phe Thr Val Leu Tyr Thr Leu Ile Asn Lys
            260                 265                 270

Ser Asn Glu Met Leu Tyr His Tyr Leu Lys Asn Arg Pro Ile Asn Gln
        275                 280                 285

Phe Thr Met Leu Asp Cys His Asp Gly Ile Pro Val Lys Pro Asp Leu
    290                 295                 300

Asp Gly Leu Ile Asp Thr Lys Lys Ala Lys Glu Val Val Asp Ile Cys
305                 310                 315                 320

Val Gln Arg Gly Ala Asn Leu Ser Leu Ile Tyr Gly Asp Lys Tyr Lys
                325                 330                 335

Ser Glu Asp Gly Phe Asp Val His Gln Ile Asn Cys Thr Tyr Tyr Ser
            340                 345                 350

Ala Leu Asn Cys Asp Asp Ala Tyr Leu Ala Ala Arg Ala Ile Gln
        355                 360                 365

Phe Phe Thr Pro Gly Ile Pro Gln Val Tyr Tyr Val Gly Leu Leu Ala
    370                 375                 380

Gly Val Asn Asp Phe Glu Ala Val Lys Lys Thr Lys Glu Gly Arg Glu
385                 390                 395                 400

Ile Asn Arg His Asn Tyr Gly Leu Lys Glu Ile Glu Glu Ser Val Gln
                405                 410                 415

Lys Asn Val Val Gln Arg Leu Lys Leu Ile Arg Phe Arg Asn Glu
            420                 425                 430

Tyr Glu Ala Phe Asn Gly Glu Phe Phe Ile Glu Asp Cys Arg Lys Asp
        435                 440                 445

Glu Ile Arg Leu Thr Trp Lys Lys Asp Asp Lys Arg Cys Ser Leu Phe
    450                 455                 460

Ile Asp Leu Lys Thr Tyr Lys Thr Thr Ile Asp Tyr Ile Asn Glu Asn
465                 470                 475                 480

Gly Glu Glu Val Lys Tyr Leu Val
```

-continued

```
                485

<210> SEQ ID NO 3
<211> LENGTH: 488
<212> TYPE: PRT
<213> ORGANISM: Artificial sequence
<220> FEATURE:
<223> OTHER INFORMATION: mutant of sucrose phosphorylase of bacterium
      Thermoanaerobacterium thermosaccharolyticum

<400> SEQUENCE: 3

Met Ala Leu Lys Asn Lys Val Gln Leu Ile Thr Tyr Pro Asp Ser Leu
1               5                   10                  15

Gly Gly Asn Leu Lys Thr Leu Asn Asp Val Leu Glu Lys Tyr Phe Ser
            20                  25                  30

Asp Val Phe Gly Gly Val His Ile Leu Pro Pro Phe Pro Ser Ser Gly
        35                  40                  45

Asp Arg Gly Phe Ala Pro Ile Thr Tyr Ser Glu Ile Glu Pro Lys Phe
    50                  55                  60

Gly Thr Trp Tyr Asp Ile Lys Lys Met Ala Glu Asn Phe Asp Ile Leu
65                  70                  75                  80

Leu Asp Leu Met Val Asn His Val Ser Arg Arg Ser Ile Tyr Phe Gln
                85                  90                  95

Asp Phe Leu Lys Lys Gly Arg Lys Ser Glu Tyr Ala Asp Met Phe Ile
            100                 105                 110

Thr Leu Asp Lys Leu Trp Lys Asp Gly Lys Pro Val Lys Gly Asp Ile
        115                 120                 125

Glu Lys Met Phe Leu Thr Arg Thr Leu Pro Tyr Ser Thr Phe Lys Ile
    130                 135                 140

Glu Glu Thr Gly Glu Glu Glu Lys Val Trp Thr Thr Phe Gly Lys Thr
145                 150                 155                 160

Asp Pro Ser Glu Gln Ile Asp Leu Asp Val Asn Ser His Leu Val Arg
                165                 170                 175

Glu Phe Leu Leu Glu Val Phe Lys Thr Phe Ser Asn Phe Gly Val Lys
            180                 185                 190

Ile Val Arg Leu Asp Ala Val Gly Tyr Val Ile Lys Lys Ile Gly Thr
        195                 200                 205

Ser Cys Phe Phe Val Glu Pro Glu Ile Tyr Glu Phe Leu Asp Trp Ala
    210                 215                 220

Lys Gly Gln Ala Ala Ser Tyr Gly Ile Glu Leu Leu Leu Glu Val His
225                 230                 235                 240

Ser Gln Phe Glu Val Gln Tyr Lys Leu Ala Glu Arg Gly Phe Leu Ile
                245                 250                 255

Tyr Asp Phe Ile Leu Pro Phe Thr Val Leu Tyr Thr Leu Ile Asn Lys
            260                 265                 270

Ser Asn Glu Met Leu Tyr His Tyr Leu Lys Asn Arg Pro Ile Asn Gln
        275                 280                 285

Phe Thr Met Leu Asp Cys His Asp Gly Ile Pro Val Lys Pro Asp Leu
    290                 295                 300

Asp Gly Leu Ile Asp Thr Lys Lys Ala Lys Glu Val Val Asp Ile Cys
305                 310                 315                 320

Val Gln Arg Gly Ala Asn Leu Ser Leu Ile Tyr Gly Asp Lys Tyr Lys
                325                 330                 335

Ser Glu Asp Gly Phe Asp Val His Gln Ile Asn Cys Thr Tyr Tyr Ser
            340                 345                 350
```

```
Ala Leu Asn Cys Asp Asp Ala Tyr Leu Ala Ala Arg Ala Ile Gln
            355                 360                 365

Phe Phe Thr Pro Gly Ile Pro Gln Val Tyr Tyr Val Gly Leu Leu Ala
    370                 375                 380

Gly Val Asn Asp Phe Glu Ala Val Lys Lys Thr Lys Glu Gly Arg Glu
385                 390                 395                 400

Ile Asn Arg His Asn Tyr Gly Leu Lys Glu Ile Glu Ser Val Gln
                405                 410                 415

Lys Asn Val Val Gln Arg Leu Leu Lys Leu Ile Arg Phe Arg Asn Glu
            420                 425                 430

Tyr Glu Ala Phe Asn Gly Glu Phe Phe Ile Glu Asp Cys Arg Lys Asp
        435                 440                 445

Glu Ile Arg Leu Thr Trp Lys Lys Asp Asp Lys Arg Cys Ser Leu Phe
    450                 455                 460

Ile Asp Leu Lys Thr Tyr Lys Thr Thr Ile Asp Tyr Ile Asn Glu Asn
465                 470                 475                 480

Gly Glu Glu Val Lys Tyr Leu Val
                485
```

<210> SEQ ID NO 4
<211> LENGTH: 488
<212> TYPE: PRT
<213> ORGANISM: Artificial sequence
<220> FEATURE:
<223> OTHER INFORMATION: mutant of sucrose phosphorylase of bacterium
    Thermoanaerobacterium thermosaccharolyticum

<400> SEQUENCE: 4

```
Met Ala Leu Lys Asn Lys Val Gln Leu Ile Thr Tyr Pro Asp Ser Leu
1               5                   10                  15

Gly Gly Asn Leu Lys Thr Leu Asn Asp Val Leu Glu Lys Tyr Phe Ser
            20                  25                  30

Asp Val Phe Gly Gly Val His Ile Leu Pro Pro Phe Pro Ser Ser Gly
        35                  40                  45

Asp Arg Gly Phe Ala Pro Ile Thr Tyr Ser Glu Ile Glu Pro Lys Phe
    50                  55                  60

Gly Thr Trp Tyr Asp Ile Lys Lys Met Ala Glu Asn Phe Asp Ile Leu
65                  70                  75                  80

Leu Asp Leu Met Val Asn His Val Ser Arg Arg Ser Ile Tyr Phe Gln
                85                  90                  95

Asp Phe Leu Lys Lys Gly Arg Lys Ser Glu Tyr Ala Asp Met Phe Ile
            100                 105                 110

Thr Leu Asp Lys Leu Trp Lys Asp Gly Lys Pro Val Lys Gly Asp Ile
        115                 120                 125

Glu Lys Met Phe Leu Gly Arg Thr Leu Pro Tyr Ser Thr Phe Lys Ile
    130                 135                 140

Glu Glu Thr Gly Glu Glu Glu Lys Val Trp Thr Thr Phe Gly Lys Thr
145                 150                 155                 160

Asp Pro Ser Glu Gln Ile Asp Leu Asp Val Asn Ser His Leu Val Arg
                165                 170                 175

Glu Phe Leu Leu Glu Val Phe Thr Phe Ser Asn Phe Gly Val Lys
            180                 185                 190

Ile Val Arg Leu Asp Ala Val Gly Tyr Val Ile Lys Lys Ile Gly Thr
        195                 200                 205

Ser Cys Phe Phe Val Glu Pro Glu Ile Tyr Glu Phe Leu Asp Trp Ala
    210                 215                 220
```

Lys Gly Gln Ala Ala Ser Tyr Gly Ile Glu Leu Leu Glu Val His
225                 230                 235                 240

Ser Gln Phe Glu Val Gln Tyr Lys Leu Ala Glu Arg Gly Phe Leu Ile
            245                 250                 255

Tyr Asp Phe Ile Leu Pro Phe Thr Val Leu Tyr Thr Leu Ile Asn Lys
                260                 265                 270

Ser Asn Glu Met Leu Tyr His Tyr Leu Lys Asn Arg Pro Ile Asn Gln
            275                 280                 285

Phe Thr Met Leu Asp Cys His Asp Gly Ile Pro Val Lys Pro Asp Leu
290                 295                 300

Asp Gly Leu Ile Asp Thr Lys Lys Ala Lys Glu Val Val Asp Ile Cys
305                 310                 315                 320

Val Gln Arg Gly Ala Asn Leu Ser Leu Ile Tyr Gly Asp Lys Tyr Lys
                325                 330                 335

Ser Glu Asp Gly Phe Asp Val His Gln Ile Asn Cys Thr Tyr Tyr Ser
            340                 345                 350

Ala Leu Asn Cys Asp Asp Ala Tyr Leu Ala Ala Arg Ala Ile Gln
            355                 360                 365

Phe Phe Thr Pro Gly Ile Pro Gln Val Tyr Tyr Val Gly Leu Leu Ala
370                 375                 380

Gly Val Asn Asp Phe Glu Ala Val Lys Lys Thr Lys Glu Gly Arg Glu
385                 390                 395                 400

Ile Asn Arg His Asn Tyr Gly Leu Lys Glu Ile Glu Glu Ser Val Gln
                405                 410                 415

Lys Asn Val Val Gln Arg Leu Leu Lys Leu Ile Arg Phe Arg Asn Glu
            420                 425                 430

Tyr Glu Ala Phe Asn Gly Glu Phe Phe Ile Glu Asp Cys Arg Lys Asp
            435                 440                 445

Glu Ile Arg Leu Thr Trp Lys Lys Asp Asp Lys Arg Cys Ser Leu Phe
450                 455                 460

Ile Asp Leu Lys Thr Tyr Lys Thr Thr Ile Asp Tyr Ile Asn Glu Asn
465                 470                 475                 480

Gly Glu Glu Val Lys Tyr Leu Val
                485

<210> SEQ ID NO 5
<211> LENGTH: 487
<212> TYPE: PRT
<213> ORGANISM: Artificial sequence
<220> FEATURE:
<223> OTHER INFORMATION: mutant of sucrose phosphorylase of bacterium
      Thermoanaerobacterium thermosaccharolyticum

<400> SEQUENCE: 5

Met Ala Leu Lys Asn Lys Val Gln Leu Ile Thr Tyr Pro Asp Ser Leu
1               5                   10                  15

Gly Gly Asn Leu Lys Thr Leu Asn Asp Val Leu Glu Lys Tyr Phe Ser
            20                  25                  30

Asp Val Phe Gly Gly Val His Ile Leu Pro Pro Phe Pro Ser Ser Gly
        35                  40                  45

Asp Arg Gly Phe Ala Pro Ile Thr Tyr Ser Glu Ile Glu Pro Lys Phe
    50                  55                  60

Gly Thr Trp Tyr Asp Ile Lys Lys Met Ala Glu Asn Phe Asp Ile Leu
65                  70                  75                  80

Leu Asp Leu Met Val Asn His Val Ser Arg Arg Ser Ile Tyr Phe Gln

```
                    85                  90                  95
Asp Phe Leu Lys Lys Gly Arg Lys Ser Glu Tyr Ala Asp Met Phe Ile
                100                 105                 110

Thr Leu Asp Lys Leu Trp Lys Asp Gly Lys Pro Val Lys Gly Asp Ile
            115                 120                 125

Glu Lys Met Phe Leu Arg Thr Leu Pro Tyr Ser Thr Phe Lys Ile Glu
        130                 135                 140

Glu Thr Gly Glu Glu Lys Val Trp Thr Thr Phe Gly Lys Thr Asp
145                 150                 155                 160

Pro Ser Glu Gln Ile Asp Leu Asp Val Asn Ser His Leu Val Arg Glu
                165                 170                 175

Phe Leu Leu Glu Val Phe Lys Thr Phe Ser Asn Phe Gly Val Lys Ile
                180                 185                 190

Val Arg Leu Asp Ala Val Gly Tyr Val Ile Lys Lys Ile Gly Thr Ser
                195                 200                 205

Cys Phe Phe Val Glu Pro Glu Ile Tyr Glu Phe Leu Asp Trp Ala Lys
            210                 215                 220

Gly Gln Ala Ala Ser Tyr Gly Ile Glu Leu Leu Glu Val His Ser
225                 230                 235                 240

Gln Phe Glu Val Gln Tyr Lys Leu Ala Glu Arg Gly Phe Leu Ile Tyr
                245                 250                 255

Asp Phe Ile Leu Pro Phe Thr Val Leu Tyr Thr Leu Ile Asn Lys Ser
            260                 265                 270

Asn Glu Met Leu Tyr His Tyr Leu Lys Asn Arg Pro Ile Asn Gln Phe
        275                 280                 285

Thr Met Leu Asp Cys His Asp Gly Ile Pro Val Lys Pro Asp Leu Asp
    290                 295                 300

Gly Leu Ile Asp Thr Lys Lys Ala Lys Glu Val Val Asp Ile Cys Val
305                 310                 315                 320

Gln Arg Gly Ala Asn Leu Ser Leu Ile Tyr Gly Asp Lys Tyr Lys Ser
                325                 330                 335

Glu Asp Gly Phe Asp Val His Gln Ile Asn Cys Thr Tyr Tyr Ser Ala
            340                 345                 350

Leu Asn Cys Asp Asp Ala Tyr Leu Ala Ala Arg Ala Ile Gln Phe
        355                 360                 365

Phe Thr Pro Gly Ile Pro Gln Val Tyr Val Gly Leu Leu Ala Gly
    370                 375                 380

Val Asn Asp Phe Glu Ala Val Lys Lys Thr Lys Glu Gly Arg Glu Ile
385                 390                 395                 400

Asn Arg His Asn Tyr Gly Leu Lys Glu Ile Glu Ser Val Gln Lys
                405                 410                 415

Asn Val Val Gln Arg Leu Leu Lys Leu Ile Arg Phe Arg Asn Glu Tyr
            420                 425                 430

Glu Ala Phe Asn Gly Glu Phe Phe Ile Glu Asp Cys Arg Lys Asp Glu
        435                 440                 445

Ile Arg Leu Thr Trp Lys Lys Asp Lys Arg Cys Ser Leu Phe Ile
    450                 455                 460

Asp Leu Lys Thr Tyr Lys Thr Thr Ile Asp Tyr Ile Asn Glu Asn Gly
465                 470                 475                 480

Glu Glu Val Lys Tyr Leu Val
                485

<210> SEQ ID NO 6
```

```
<211> LENGTH: 488
<212> TYPE: PRT
<213> ORGANISM: Artificial sequence
<220> FEATURE:
<223> OTHER INFORMATION: mutant of sucrose phosphorylase of bacterium
      Thermoanaerobacterium thermosaccharolyticum
<220> FEATURE:
<221> NAME/KEY: MISC_FEATURE
<222> LOCATION: (134)..(134)
<223> OTHER INFORMATION: X represents A,V,T or G

<400> SEQUENCE: 6
```

Met Ala Leu Lys Asn Lys Val Gln Leu Ile Thr Tyr Pro Asp Ser Leu
1               5                   10                  15

Gly Gly Asn Leu Lys Thr Leu Asn Asp Val Leu Glu Lys Tyr Phe Ser
            20                  25                  30

Asp Val Phe Gly Gly Val His Ile Leu Pro Pro Phe Pro Ser Ser Gly
        35                  40                  45

Asp Arg Gly Phe Ala Pro Ile Thr Tyr Ser Glu Ile Glu Pro Lys Phe
    50                  55                  60

Gly Thr Trp Tyr Asp Ile Lys Lys Met Ala Glu Asn Phe Asp Ile Leu
65                  70                  75                  80

Leu Asp Leu Met Val Asn His Val Ser Arg Arg Ser Ile Tyr Phe Gln
                85                  90                  95

Asp Phe Leu Lys Lys Gly Arg Lys Ser Glu Tyr Ala Asp Met Phe Ile
            100                 105                 110

Thr Leu Asp Lys Leu Trp Lys Asp Gly Lys Pro Val Lys Gly Asp Ile
        115                 120                 125

Glu Lys Met Phe Leu Xaa Arg Thr Leu Pro Tyr Ser Thr Phe Lys Ile
    130                 135                 140

Glu Glu Thr Gly Glu Glu Glu Lys Val Trp Thr Thr Phe Gly Lys Thr
145                 150                 155                 160

Asp Pro Ser Glu Gln Ile Asp Leu Asp Val Asn Ser His Leu Val Arg
                165                 170                 175

Glu Phe Leu Leu Glu Val Phe Lys Thr Phe Ser Asn Phe Gly Val Lys
            180                 185                 190

Ile Val Arg Leu Asp Ala Val Gly Tyr Val Ile Lys Lys Ile Gly Thr
        195                 200                 205

Ser Cys Phe Phe Val Glu Pro Glu Ile Tyr Glu Phe Leu Asp Trp Ala
    210                 215                 220

Lys Gly Gln Ala Ala Ser Tyr Gly Ile Glu Leu Leu Leu Glu Val His
225                 230                 235                 240

Ser Gln Phe Glu Val Gln Tyr Lys Leu Ala Glu Arg Gly Phe Leu Ile
                245                 250                 255

Tyr Asp Phe Ile Leu Pro Phe Thr Val Leu Tyr Thr Leu Ile Asn Lys
            260                 265                 270

Ser Asn Glu Met Leu Tyr His Tyr Leu Lys Asn Arg Pro Ile Asn Gln
        275                 280                 285

Phe Thr Met Leu Asp Cys His Asp Gly Ile Pro Val Lys Pro Asp Leu
    290                 295                 300

Asp Gly Leu Ile Asp Thr Lys Lys Ala Lys Glu Val Val Asp Ile Cys
305                 310                 315                 320

Val Gln Arg Gly Ala Asn Leu Ser Leu Ile Tyr Gly Asp Lys Tyr Lys
                325                 330                 335

Ser Glu Asp Gly Phe Asp Val His Gln Ile Asn Cys Thr Tyr Tyr Ser
            340                 345                 350

```
Ala Leu Asn Cys Asp Asp Ala Tyr Leu Ala Ala Arg Ala Ile Gln
            355             360             365

Phe Phe Thr Pro Gly Ile Pro Gln Val Tyr Tyr Val Gly Leu Leu Ala
    370             375             380

Gly Val Asn Asp Phe Glu Ala Val Lys Lys Thr Lys Glu Gly Arg Glu
385             390             395             400

Ile Asn Arg His Asn Tyr Gly Leu Lys Glu Ile Glu Glu Ser Val Gln
            405             410             415

Lys Asn Val Val Gln Arg Leu Leu Lys Leu Ile Arg Phe Arg Asn Glu
            420             425             430

Tyr Glu Ala Phe Asn Gly Glu Phe Phe Ile Glu Asp Cys Arg Lys Asp
        435             440             445

Glu Ile Arg Leu Thr Trp Lys Lys Asp Asp Lys Arg Cys Ser Leu Phe
        450             455             460

Ile Asp Leu Lys Thr Tyr Lys Thr Thr Ile Asp Tyr Ile Asn Glu Asn
465             470             475             480

Gly Glu Glu Val Lys Tyr Leu Val
                485
```

MUTANT SUCROSE PHOSPHORYLASES WITH IMPROVED GLYCOSYLATION ACTIVITY TOWARDS POLYPHENOLS

TECHNICAL FIELD OF INVENTION

The present invention relates to glycosylating polyphenols via biocatalysis. More specifically the present invention discloses particular mutants of the thermostable sucrose phosphorylase derived from the microorganism *Thermoanaerobacterium thermosaccharolyticum* which efficiently glycosylate polyphenols such as resveratrol.

BACKGROUND ART

Polyphenols are natural products with important applications in the cosmetic, pharmaceutical and food industry (Quideau et al., 2011; Espín et al., 2007). In particular, resveratrol (3,5,4'-trihydroxystilbene) is seen as a very interesting compound, since several studies reported it to be anti-carcinogenic, anti-inflammatory, anti-microbial and even to expand man's life-span (Frémont, 2000; Novelle et al., 2015; Park and Pezzuto, 2015; Biagi and Bertelli, 2015). Glycosylation of resveratrol can dramatically improve its solubility and bioavailability, but the effect differs with the type of glycosidic bond (Thuan and Sohng, 2013; Torres et al., 2011; Ozaki et al., 2011). For example, the 3-α-glucoside of resveratrol was found to be more soluble than the 3-β-glucoside (Torres et al., 2011). For stereo- and regiospecific glycosylation, the advantages of biocatalysis over chemical processes are obvious (de Roode et al., 2003; Desmet et al., 2012; Bornscheuer et al., 2013).

Most glycosyl transferases require nucleotide-activated donor substrates (e.g. UDP-Glc), which are rather expensive for large-scale applications (Bungaruang et al., 2013; Breton et al., 2012; Gantt et al., 2011; Palcic, 2011; Lairson et al., 2008). However, a few enzymes are able to catalyze transglycosylation reactions starting from simple sugars like maltodextrins (e.g. CGTase) or sucrose (e.g. glucansucrase) (Desmet et al., 2012). Similarly, sucrose phosphorylase (SP, EC 2.4.1.7) can transfer the glucose moiety of sucrose to a variety of acceptors through a double displacement mechanism (Puchart, 2015; Desmet and Soetaert, 2012; Goedl et al., 2008; Aerts, Verhaeghe, Roman, Stevens, Desmet and Soetaert, 2011a). It should be noted that sucrose not only is cheap but also very reactive, with an energy content that is comparable with that of nucleotide sugars (Monsan et al., 2010). High yields can thus be obtained, as has been reported for the production of 2-O-alpha-D-glucopyranosyl-sn-glycerol, a moisturizing agent in cosmetics commercialized under the tradename Glycoin® (Goedl et al., 2008).

Unfortunately, the activity of SP on (poly)phenolic acceptors is very low, even barely detectable in most cases (Aerts, Verhaeghe, Roman, Stevens, Desmet and Soetaert, 2011b; Kitao et al., 2014; De Winter et al., 2014; De Winter et al., 2013). It has been suggested that the main problem is the enzyme's low affinity for such compounds, which cannot be compensated by increasing the acceptor concentrations because of their low solubility (De Winter et al., 2013; Aerts, Verhaeghe, Roman, Stevens, Desmet and Soetaert, 2011a). Although increased transglycosylation rates have been reported upon addition of organic solvents (De Winter et al., 2014; De Winter et al., 2013). However, saturation of the enzyme has never been achieved and productivity has generally remained too low for practical applications. With resveratrol, for example, the best result has been obtained in 20% of the ionic liquid AMMOENG™ 101, but that only generated 3 mM of resveratrol 3-alpha-glucoside (De Winter et al., 2013). Therefore, there is an urgent need to find or design an SP capable of efficiently glycosylating polyphenols such as resveratrol.

Two (thermo)stable SP enzymes have so far been identified, i.e. one in *Bifidobacterium adolescentis* (BaSP, Cerdobbel et al., 2011; WO2011/124538) and one in *Thermoanaerobacterium thermosaccharolyticum* (TtSPP, WO2014/060452). The latter enzyme actually prefers sucrose 6'-phosphate as substrate (EC 2.4.1.329) but can still efficiently use sucrose as glycosyl donor ($K_m$=77 mM) (Verhaeghe et al., 2014). The latter authors further disclosed a R134A variant of TtSPP, which was shown to play a role in the binding of sucrose-6'-phosphate or fructose-6-phosphate.

DESCRIPTION OF INVENTION

The present invention discloses improved variants, such as TtSPP_R134A, that can be used for the efficient glycosylation of polyphenols such as resveratrol at gram scales. Indeed, these new biocatalysts are able to (i) reach full and specific conversion of resveratrol in (ii) an aqueous system without the need for solvent additions and (iii) using sucrose as cheap and renewable glycosyl donor. However, it is clear that the variant's improved efficiency is not limited to resveratrol but is also demonstrated on several large acceptors, thereby revealing a substrate promiscuity that is useful for practical applications in various industrial sectors.

Therefore, the present invention relates to an in vitro method to glycosylate a polyphenol comprising:
- contacting in vitro a sucrose phosphorylase comprising the amino acid sequence of SEQ ID No 1 (=variant R134A of TtSPP), SEQ ID No 2 (=variant R134V of TtSPP), SEQ ID No 3 (=variant R134T of TtSPP), SEQ ID No 4 (variant R134G of TtSPP) or SEQ ID No 5 (=variant of TtSPP wherein R134 is deleted) with sucrose (or alternatively with alpha-glucose-1-phosphate) and a polyphenol, and
- glycosylating said polyphenol.

SEQ ID No 1 is the following amino acid sequence (A134 is indicated in bold & underlined):

MALKNKVQLITYPDSLGGNLKTLNDVLEKYFSDVFGGVHILPPFPSSGD

RGFAPITYSEIEPKFGTWYDIKKMAENFDILLDLMVNHVSRRSIYFQDF

LKKGRKSEYADMFITLDKLWKDGKPVKGDIEKMFLARTLPYSTFKIEET

GEEEKVWTTFGKTDPSEQIDLDVNSHLVREFLLEVFKTFSNFGVKIVRL

DAVGYVIKKIGTSCFFVEPEIYEFLDWAKGQAASYGIELLLEVHSQFEV

-continued

QYKLAERGFLIYDFILPFTVLYTLINKSNEMLYHYLKNRPINQFTMLDC

HDGIPVKPDLDGLIDTKKAKEVVDICVQRGANLSLIYGDKYKSEDGFDV

HQINCTYYSALNCDDDAYLAARAIQFFTPGIPQVYYVGLLAGVNDFEAV

KKTKEGREINRHNYGLKEIEESVQKNVVQRLLKLIRFRNEYEAFNGEFF

IEDCRKDEIRLTWKKDDKRCSLFIDLKTYKTTIDYINENGEEVKYLV

SEQ ID No 2 is the following amino acid sequence (V134 is indicated in bold & underlined):

MALKNKVQLITYPDSLGGNLKTLNDVLEKYFSDVFGGVHILPPFPSSGD

RGFAPITYSEIEPKFGTWYDIKKMAENFDILLDLMVNHVSRRSIYFQDF

LKKGRKSEYADMFITLDKLWKDGKPVKGDIEKMFLVRTLPYSTFKIEET

GEEEKVWTTFGKTDPSEQIDLDVNSHLVREFLLEVFKTFSNFGVKIVRL

DAVGYVIKKIGTSCFFVEPEIYEFLDWAKGQAASYGIELLLEVHSQFEV

QYKLAERGFLIYDFILPFTVLYTLINKSNEMLYHYLKNRPINQFTMLDC

HDGIPVKPDLDGLIDTKKAKEVVDICVQRGANLSLIYGDKYKSEDGFDV

HQINCTYYSALNCDDDAYLAARAIQFFTPGIPQVYYVGLLAGVNDFEAV

KKTKEGREINRHNYGLKEIEESVQKNVVQRLLKLIRFRNEYEAFNGEFF

IEDCRKDEIRLTWKKDDKRCSLFIDLKTYKTTIDYINENGEEVKYLV

SEQ ID No 3 is the following amino acid sequence (T134 is indicated in bold & underlined):

MALKNKVQLITYPDSLGGNLKTLNDVLEKYFSDVFGGVHILPPFPSSGD

RGFAPITYSEIEPKFGTWYDIKKMAENFDILLDLMVNHVSRRSIYFQDF

LKKGRKSEYADMFITLDKLWKDGKPVKGDIEKMFLTRTLPYSTFKIEET

GEEEKVWTTFGKTDPSEQIDLDVNSHLVREFLLEVFKTFSNFGVKIVRL

DAVGYVIKKIGTSCFFVEPEIYEFLDWAKGQAASYGIELLLEVHSQFEV

QYKLAERGFLIYDFILPFTVLYTLINKSNEMLYHYLKNRPINQFTMLDC

HDGIPVKPDLDGLIDTKKAKEVVDICVQRGANLSLIYGDKYKSEDGFDV

HQINCTYYSALNCDDDAYLAARAIQFFTPGIPQVYYVGLLAGVNDFEAV

KKTKEGREINRHNYGLKEIEESVQKNVVQRLLKLIRFRNEYEAFNGEFF

IEDCRKDEIRLTWKKDDKRCSLFIDLKTYKTTIDYINENGEEVKYLV

SEQ ID No 4 is the following amino acid sequence (G134 is indicated in bold & underlined):

MALKNKVQLITYPDSLGGNLKTLNDVLEKYFSDVFGGVHILPPFPSSGD

RGFAPITYSEIEPKFGTWYDIKKMAENFDILLDLMVNHVSRRSIYFQDF

LKKGRKSEYADMFITLDKLWKDGKPVKGDIEKMFLGRTLPYSTFKIEET

GEEEKVWTTFGKTDPSEQIDLDVNSHLVREFLLEVFKTFSNFGVKIVRL

DAVGYVIKKIGTSCFFVEPEIYEFLDWAKGQAASYGIELLLEVHSQFEV

QYKLAERGFLIYDFILPFTVLYTLINKSNEMLYHYLKNRPINQFTMLDC

HDGIPVKPDLDGLIDTKKAKEVVDICVQRGANLSLIYGDKYKSEDGFDV

HQINCTYYSALNCDDDAYLAARAIQFFTPGIPQVYYVGLLAGVNDFEAV

KKTKEGREINRHNYGLKEIEESVQKNVVQRLLKLIRFRNEYEAFNGEFF

IEDCRKDEIRLTWKKDDKRCSLFIDLKTYKTTIDYINENGEEVKYLV

SEQ ID No 5 is the following amino acid (amino acid 134 of TtSPP is deleted):

MALKNKVQLITYPDSLGGNLKTLNDVLEKYFSDVFGGVHILPPFPSSGD

RGFAPITYSEIEPKFGTWYDIKKMAENFDILLDLMVNHVSRRSIYFQDF

LKKGRKSEYADMFITLDKLWKDGKPVKGDIEKMFLRTLPYSTFKIEETG

EEEKVWTTFGKTDPSEQIDLDVNSHLVREFLLEVFKTFSNFGVKIVRLD

AVGYVIKKIGTSCFFVEPEIYEFLDWAKGQAASYGIELLLEVHSQFEVQ

YKLAERGFLIYDFILPFTVLYTLINKSNEMLYHYLKNRPINQFTMLDCH

DGIPVKPDLDGLIDTKKAKEVVDICVQRGANLSLIYGDKYKSEDGFDVH

QINCTYYSALNCDDDAYLAARAIQFFTPGIPQVYYVGLLAGVNDFEAVK

KTKEGREINRHNYGLKEIEESVQKNVVQRLLKLIRFRNEYEAFNGEFFI

EDCRKDEIRLTWKKDDKRCSLFIDLKTYKTTIDYINENGEEVKYLV

The term polyphenol' relates to hydroxylated molecules that contain at least two benzene rings. The latter polyphenols comprise the flavonoids and stilbenoids. The structural formula of the latter polyphenols and specific, representatives is/are the following:

Structural skeleton of FLAVONOIDS:
5-carbon skeleton, which consists or two phenyl rings (A and B) and heterocyclic ring (C)

| | |
|---|---|
| Flavones: | variing hydroxyl groups at ring A and/or B [e.g. apigenine = 4',5,7-trihydroxyflavone] |
| Flavanones: | flavone-structure lacking double bond in ring C (1) [e.g. hesperetin = 3',5,7-trihydroxy-4'-methoxyflavanone] |
| Flavonols: | flavone-structure with a hydroxylated ring C (2) [e.g. quercetin = 3,3',4',5,7-pentahydroxyflavone] |
| Catechins: | flavone-structure lacking the keto-group (3) and double bond (1) in ring C but holding a hydroxyl group at (2) [e.g.epicatechin = (−) −3,3', 4', 5,7-flavanpentol] |

Structural skeleton of STILBENOIDS:
2 phenyl rings (A and B) connected via an ethene double bond (structure known as stilbene) being polyhydroxylated at the phenyl rings
main representative: resveratrol = trans-3,4',5-trihydroxystilbene wherein R is at least one H and/or attached glycosides.

Therefore, the present invention further specifically relates to an in vitro as indicated above method wherein said polyphenol is a stilbenoid, an in vitro method as indicated above wherein said stilbenoid is resveratrol, an in vitro method as indicated above wherein said polyphenol is a flavonoid, and an in vitro method as indicated above wherein said flavonoid is apigenine, hesperetin, quercetin or epicatechin.

Moreover the present invention relates to an in vitro as indicated above wherein said polyphenol is a phenoxyphenol having the following structural formula:

wherein R is at least one H and/or attached glycosides

The present invention further relates to an in vitro method as described above wherein said sucrose phosphorylase is a fragment of SEQ ID No 1, 2, 3, 4 or 5, wherein said fragment comprises, in addition to having the amino acid A, V, T or G at position 134 of SEQ ID No 1-4, respectively, or having a deletion at position 134 as shown by SEQ ID No 5, at least the 16 catalytic amino acids on the amino acid positions as shown in SEQ ID No 6.

SEQ ID No 6 is thus the amino acid sequence of TtSPP indicating in bold the 16 catalytic amino acids of TtSPP in addition to X on position 134 of SEQ ID No 1-4, wherein X=the amino acid A, V, T or G at position 134 of SEQ ID No 1-4, or is deleted as shown by SEQ ID No 5:

has at least 90% sequence identity with SEQ ID No 1, 2, 3, 4 or 5 and wherein said fragment comprises, in addition to having the amino acid A, V, T or G at position 134 of SEQ ID No 1-4, respectively, or having a deletion at position 134 as shown by SEQ ID No 5, at least the following 16 catalytic amino acids of SEQ ID No 6: D49, F52, H87, F157, Q165, R195, D197, A198, Y201, E238, H240, H295, D296, D342, Q345 and R399.

The terms 'at least 90% sequence identity' refers to a sequence identity of 90, 91, 92, 93, 94, 95, 96, 97, 98, 99 or 100% sequence identity with SEQ ID No 1, 2, 3, 4 or 5.

The present invention further relates to a variant of the thermostable sucrose phosphorylase derived from the microorganism Thermoanaerobacterium thermosaccharolyticum comprising SEQ ID No 2, 3, 4 or 5, or, comprising a fragment as defined above.

EXAMPLES

Materials & Methods
Chemicals.
All chemicals were of analytical grades and purchased either from Sigma-Aldrich or Carbosynth.
Cloning, Expression and Mutagenesis.
Vector constructs for heterologous expression of BaSP- and TtSPP-gene sequences, as well as the designed variants, were inserted into the pCXP34h vector and continuously expressed in E. coli BL21 cells as previously described

```
MALKNKVQLITYPDSLGGNLKTLNDVLEKYFSDVFGGVHILPPFPSSGDRGFAPITYSEIEPKFGTWYDIKKMAENFDILLDLMVN

HVSRRSIYFQDFLKKGRKSEYADMFITLDKLWKDGKPVKGDIEKMFLXRTLPYSTFKIEETGEEEKVWTIFGKTDPSEQIDLDVNS

HLVREFLLEVFKTFSNFGVKIVRLDAVGYVIKKIGTSCFFVEPEIYEFLDWAKGQAASYGIELLLEVHSQFEVQYKLAERGFLIYDFIL

PFTVLYTLINKSNEMLYHYLKNRPINQFTMLDCHDGIPVKPDLDGLIDTKKAKEVVDICVQRGANLSLIYGDKYKSEDGFDVHQIN

CTYYSALNCDDDAYLAARAIQFFTPGIPQVYYVGLLAGVNDFEAVKKTKEGREINRHNYGLKEIEESVQKNVVQRLLKLIRFRNEYE

AFNGEFFIEDCRKDEIRLTWKKDDKRCSLFIDLKTYKTTIDYINENGEEVKYLV
```

In other words, the present invention relates to an in vitro method to glycosylate a polyphenol comprising:
contacting in vitro a sucrose phoshorylase with sucrose or alpha-glucose-1 phosphate, and, a polyphenol, and, glycosylating said polyphenol, wherein said sucrose phoshorylase is a fragment of SEQ ID No 1, 2, 3, 4 or 5 wherein said fragment comprises, in addition to having the amino acid A, V, T or G at position 134 of SEQ ID No 1-4, respectively, or having a deletion at position 134 as shown by SEQ ID No 5, at least the following 16 catalytic amino acids of SEQ ID No 6: D49, F52, H87, F157, Q165, R195, D197, A198, Y201, E238, H240, H295, D296, D342, Q345 and R399.

The terms 'a fragment of SEQ ID No 1, 2, 3, 4 or 5' refer to a part of SEQ ID No 1, 2, 3, 4 or 5 containing less amino acids than SEQ ID No 1, 2, 3, 4 or 5 and that has 100% sequence identity with SEQ ID No 1, 2, 3, 4 or 5.

More specifically, the present invention relates to an in vitro method to glycosylate a polyphenol comprising:
contacting in vitro a sucrose phosphorylase with sucrose or alpha-glucose-1 phosphate, and, a polyphenol, and, glycosylating said polyphenol, wherein said sucrose phoshorylase is a fragment of SEQ ID No 1, 2, 3, 4 or 5 that (Verhaeghe et al, 2014). Site-specific mutations were introduced using phosphorylated primers for whole plasmid PCRs and successive ligation. Generation of the single site-saturation library of position R134 was done likewise using a whole plasmid amplification method with NNK-degeneracy primers. Successful randomization and final plasmids were checked by sequencing.

Protein Extraction and Purification.

Recombinant proteins were produced and heat-purified as previously described (Cerdobbel et al, 2010). Crude protein extracts for screening purposes were generated by exposing frozen cell pellets from production cultures to lysis buffer (50 mM MOPS-buffer, 50 mM $Na_2SO_4$, 4 mM $MgSO_4$, 1 mM EDTA, 1 $gL^{-1}$ lysozyme, 100 μM PMSF, pH 7.5) for 30 min at 37° C. Supernatants after centrifugation were assigned as crude protein extracts. Protein contents were determined according to Bradford using BSA as standard. All proteins were stored at 4° C. until further usage.

Screening Assays.

Heat-purified proteins (for tests on different acceptors) or crude protein extracts (for library screening) were incubated to a final concentration of 1 $gL^{-1}$ with 10 $gL^{-1}$ acceptor and 1 M sucrose in 50 mM MOPS-buffer at pH 6.5. Assays were performed at 37° C. in microtiterplates shaking at 200 rpm. The product amounts were evaluated after 16 h by semi-quantitative TLC-analysis: 1 µl of each sample solution was spotted on a Silica-plate (TLC-Silica gel 60 F254, Merck Millipore) and run in a solvent system from ethylacetate:methanol:water (30:5:4, v/v/v). Plates were oxidized with 10% sulphuric acid and spot intensities were determined using ImagaJ.

Enzyme Kinetics.

Kinetics of enzyme variants on resveratrol were determined in an aqueous system containing 20% ionic liquid AMMOENG 101 (kindly provided by Evonik Industries AG) to dissolve the acceptor in a range of 0 to 200 mM. At this concentration of ionic liquid, the kinetic parameters of the enzyme for its natural substrates are not affected. Reactions were started combining 8.5 µM heat purified enzymes, 1 M sucrose and the respective acceptor-concentration at 55° C. To determine the initial velocity, samples were taken every 15 minutes for one hour, and inactivated by ten-fold dilution in pure ethanol. Product formation was again quantified by TLC and ImageJ analysis, using purified resveratrol 3-alpha-glucoside as TLC-standard and a respective standard curve for calculations. Kinetic parameters were calculated by non-linear regression of the Michaelis-Menten equation with Sigma Plot v13.0. All experiments were performed in triplicate to obtain kinetic parameters as reproducible mean values±standard errors.

Production and Purification of Resveratrol 3-alpha-glucoside.

Up-scaling of the transglycosylation reactions on resveratrol was performed up to 400 ml volumes. Reactors were stirred continuously at 55° C. for 24 h, and contained 1 M sucrose, 1 mgL$^{-1}$ enzyme and 10 gL$^{-1}$ of resveratrol (suspension) in 50 mM MOPS-buffer pH 6.5. Thanks to the quantitative conversion of resveratrol, its glucoside could be simply isolated by repeated ethylacetate extractions to a purity of >90%. The solvent was evaporated and the dried product analyzed by HPLC to determine purity and yield. To verify the identity of the compound by NMR and to produce the standards (TLC, HPLC), further purification was performed by column chromatography on silica gel (EtOAC:MeOH:H$_2$O; 30:5:4; v/v/v) as described earlier (De Winter et al, 2013).

HPLC Analysis.

Reactions were followed for 24 h. Samples were taken at several time points by inactivating aliquots at 100° C. for 10 min, followed by centrifugation. Supernatants were filtered through a 0.2 µm polystyrol filter, diluted in DMSO and analyzed by HPLC using a polar Waters XBridge Amide column (250×4.6 mm, 3.5 µm) and an Alltech 2000ES ELSD-detector (40° C., gas flow 1.5 Lmin$^{-1}$), supplied with a gradient mixture of eluent A (acetonitrile, 0.2% triehtylamine) and eluent B (0.2% triethylamine): 90% solvent A (6 min), 10-25% solvent B (stepwise, 3% min$^{-1}$), 25% solvent B (20 min) and 90% solvent A (10 min). Concentrations of ingredients and respective yields were calculated according to standards of fructose, glucose and resveratrol 3-alpha-glucoside.

NMR Analysis of the Resveratrol 3-alpha-glucoside.

The chemical structure of the purified resveratrol glycoside was inferred from the combination of 1D NMR ($^1$H NMR and $^{13}$C NMR) and 2D NMR (gCOSY, gHSQC and gHMBC) spectroscopic analysis; J values are given in Hz.

$\delta_H$(400 MHz; CD$_3$OD) 7.39 (2H, d, J=8.6, 2'-H and 6'-H), 7.04 (1H, d, J=16.3, 8-H), 6.87 (1H, d, J=16.3, 7-H), 6.86 (1H, s, 2-H), 6.80 (2H, d, J=8.6, 3'-H and 5'-H), 6.62 (1H, s, 6-H), 6.54 (1H, s, 4-H), 5.50 (1H, d, J=3.5, 1"-H), 3.87 (1H, dd, J=9.7 and 8.9, 3"-H), 3.76 (2H, m, 6"-Ha, 6"-Hb), 3.72 (1H, ddd, J=9.7, 4.2 and 2.5, 5"-H), 3.60 (1H, dd, J=9.7 and 3.6, 2"-H) and 3.48 (1H, dd, J=9.7 and 8.9, 4"-H).

$\delta_C$(100 MHz; CD$_3$OD) 160.23 (C-3), 159.87 (c-5), 158.73 (C-4), 141.75 (C-1), 130.63 (C-1'), 130.25 (C-8), 129.18 (C-2' and C-6'), 127.01 (C-7), 116.83 (C-3' and C-5'), 108.70 (C-6), 107.85 (C-2), 104.88 (C-4), 99.61 (C-1"), 75.28 (C-3"), 74.63 (C-5"), 73.64 (C-2"), 71.81 (C-4"), 62.63 (C-6").

According to the COSY experiment, the proton spectrum displays a —CH=CH-group, AA'BB' and AMX spin systems of para-disubstituted and 1,3,5-trisubstituted aromatic rings, and one saccharide unit. The set of extracted vicinal constants (d, J=3.5 Hz) identified α-glucose, while the magnitude of J$_{7-H, 8-H}$ (16.3 Hz) proved the trans-conformation of resveratrol. The position of the glycosylation was confirmed by the HMBC contact of the C-3 with 1"-H.

Results

Two (thermo)stable SP enzymes have so far been identified, i.e. one in *Bifidobacterium adolescentis* (BaSP) and one in *Thermoanaerobacterium thermosaccharolyticum* (TtSPP).[9] The latter actually prefers sucrose 6'-phosphate as substrate (EC 2.4.1.329) but can still efficiently use sucrose as glycosyl donor (K$_m$=77 mM).[9b] Neither of these enzymes display significant activity on resveratrol or other polyphenolic compounds as acceptor.

Figure 1:
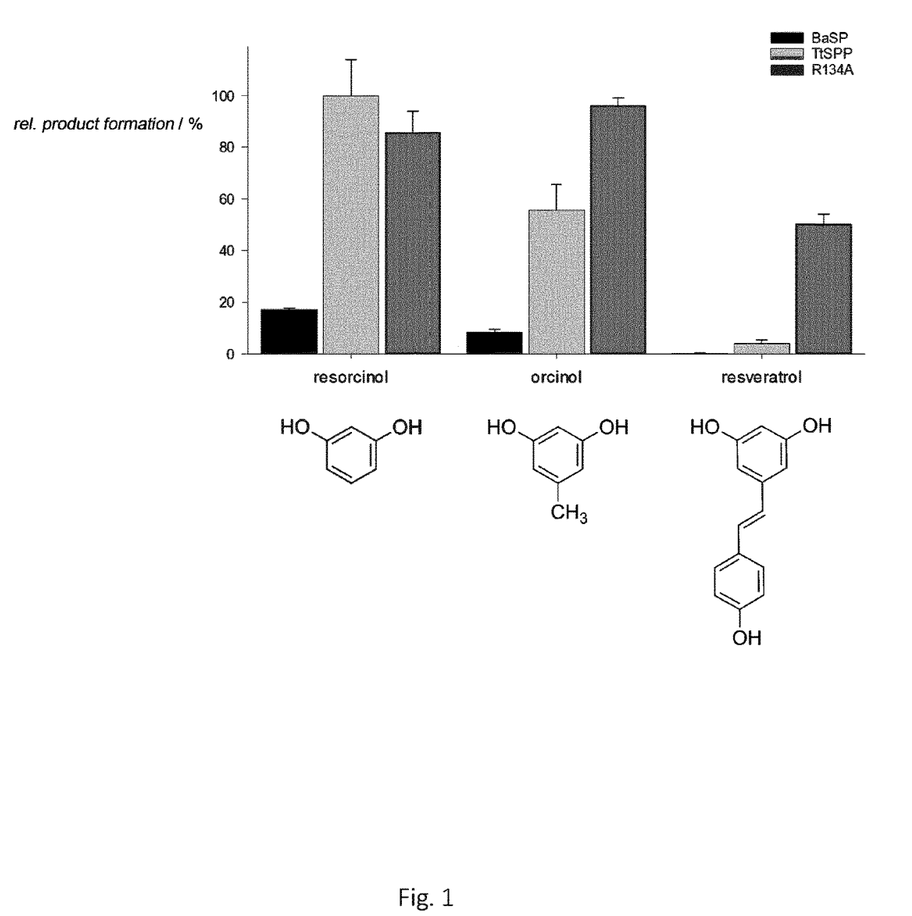
FIG. 1. Comparing transglycosylation activity of BaSP, TtSPP and R134A on resveratrol and its building blocks resorcinol and orcinol.

We tested the corresponding R134A variant for transglycosylation activity on resveratrol and smaller building blocks (FIG. 1). Effectively, the gradual decrease in activity from resorcinol>orcinol>resveratrol observed with the wild-type enzyme was almost balanced with the variant, which retained more than half of its activity on resveratrol. Site-saturation mutagenesis of position 134 did not yield variants that were better than R134A, but other small amino acids like valine and threonine also offered increased activities compared to the wild-type arginine. This confirmed our hypothesis that a bulky side chain limits binding of large acceptors in the active site of SP. However, this only was valid for position 134, since mutating other residues at the active-site entrance (e.g. K301 or H344) to alanine did not have a similar effect.

Interestingly, the unbolted R134 variants enabled us to determine kinetic parameters for the glycosylation of resveratrol (Table 1), which has never been possible with the wild-type enzyme. These measurements revealed that the affinity for resveratrol is quite reasonable, with K$_m$-values in the range of 50-200 mM. As expected, the improvements in accessibility strongly influence the k$_{cat}$-value, which gradually increases to 2.4 s$^{-1}$ when smaller side chains are introduced at position 134. The highest catalytic efficiency (12.8 M$^{-1}$ s$^{-1}$) is observed with variant R134A, which thus is the enzyme of choice for application in glycoside synthesis.

TABLE 1

Kinetic parameters of TtSPP variants for resveratrol glycosylation[a]

| enzyme | K$_m$ [mM] | k$_{cat}$ [s$^{-1}$] | k$_{cat}$/K$_m$ [M$^{-1}$ s$^{-1}$] |
|---|---|---|---|
| R134A | 185 ± 32 | 2.36 ± 0.25 | 12.8 ± 2.6 |
| R134V | 110 ± 9 | 0.45 ± 0.02 | 4.1 ± 0.4 |
| R134T | 56 ± 8 | 0.08 ± 0.004 | 1.4 ± 0.2 |

[a]Using as co-substrate 1M sucrose at pH 6.5 and 55° C.

Figure 2:
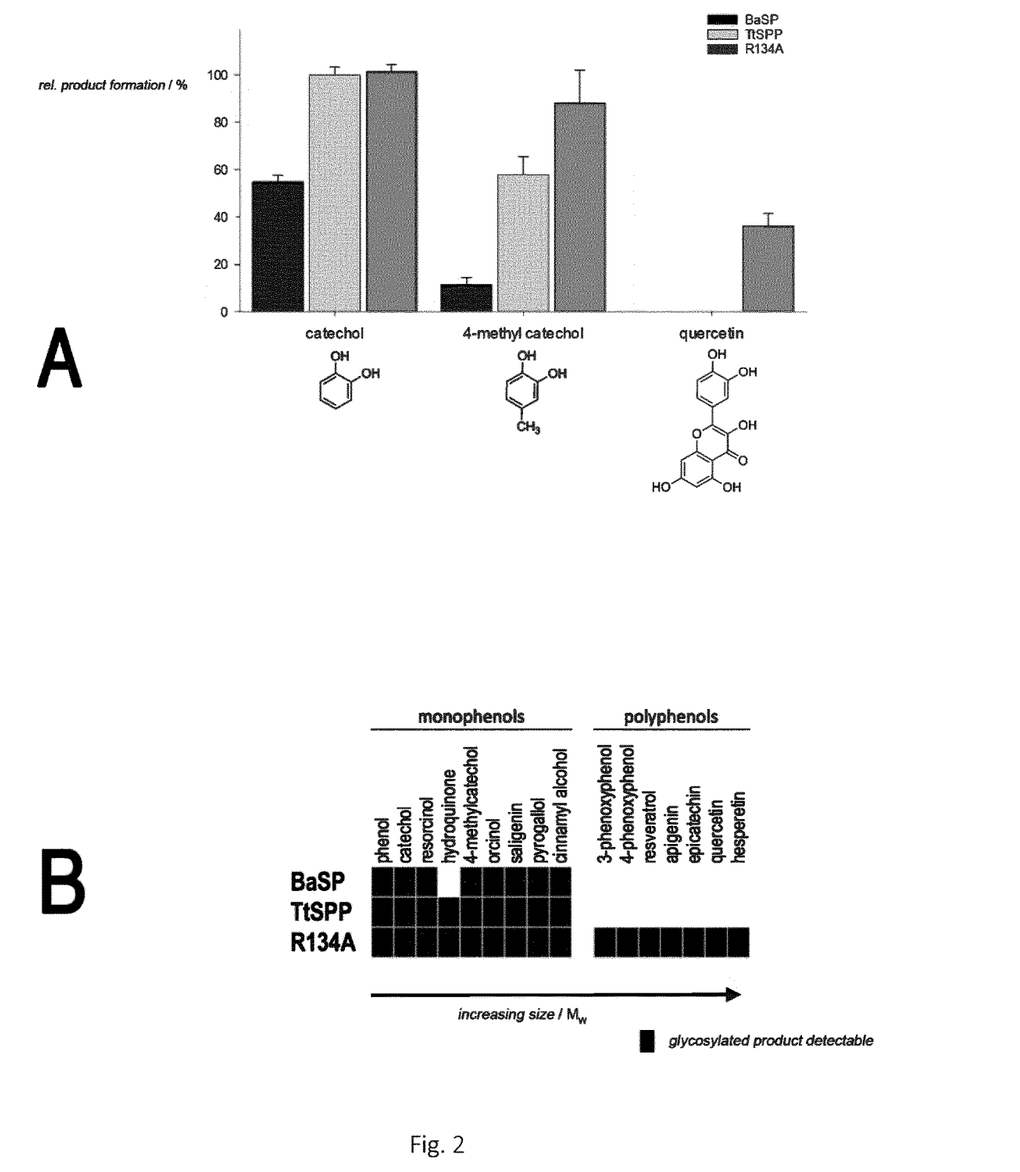
FIG. 2. Acceptor promiscuity of TtSPP and R134A compared to BaSP. (A) Semi-quantitative comparison of transglycosylation of catechol, 4-methyl catechol and quercetin. (B) Qualitative survey of promiscuity on diverse mono- and polyphenolic acceptors. (C) Structural skeleton of natural polyphenols.

The improved accessibility of the active site should be not exclusive for resveratrol but should also be noticeable with other large acceptors. Therefore, variant R134A was tested on a variety of (poly)phenols to evaluate its full promiscuity and potential as biocatalyst. Similar to the meta-benzenediol series (resorcinol-orcinol-resveratrol) shown in FIG. 1, a gradual decrease in activity with the ortho-benzenediol series (catechol>4-methyl catechol>quercetin) was again observed for the wildtype enzymes (FIG. 2 A). Also in this case, TtSPP showed higher transglycosylation activities than BaSP on the smaller compounds, but neither had activity on quercetin, a bulky representative of the flavonol class. In contrast, significant amounts of transglycosylation product could be detected with variant R134A, which confirms the enzyme's improved ability to bind larger acceptors thanks to its unbolted active site.

When comparing these three enzymes on more phenolic acceptors, the increased promiscuity of R134A towards large molecules became even more obvious (FIG. 2 B). Indeed, the latter displayed activity on structures from all five major classes of flavonoids (apigenin, epicatechin, quercetin and hesperetin) but also on artificial polyphenolics like phenoxyphenols (FIG. 2 C) in contrast to TtSPP and BaSP, respectively. This screening experiment demonstrates that variant R134A is a promiscuous biocatalyst that can be used for the glycosylation of several polyphenolic compounds of industrial relevance. Hence, this new enzyme is a very promising target for further engineering as it has opened up the potential to discover and exploit novel identities, properties and applications of glycosylated products.

Figure 3:
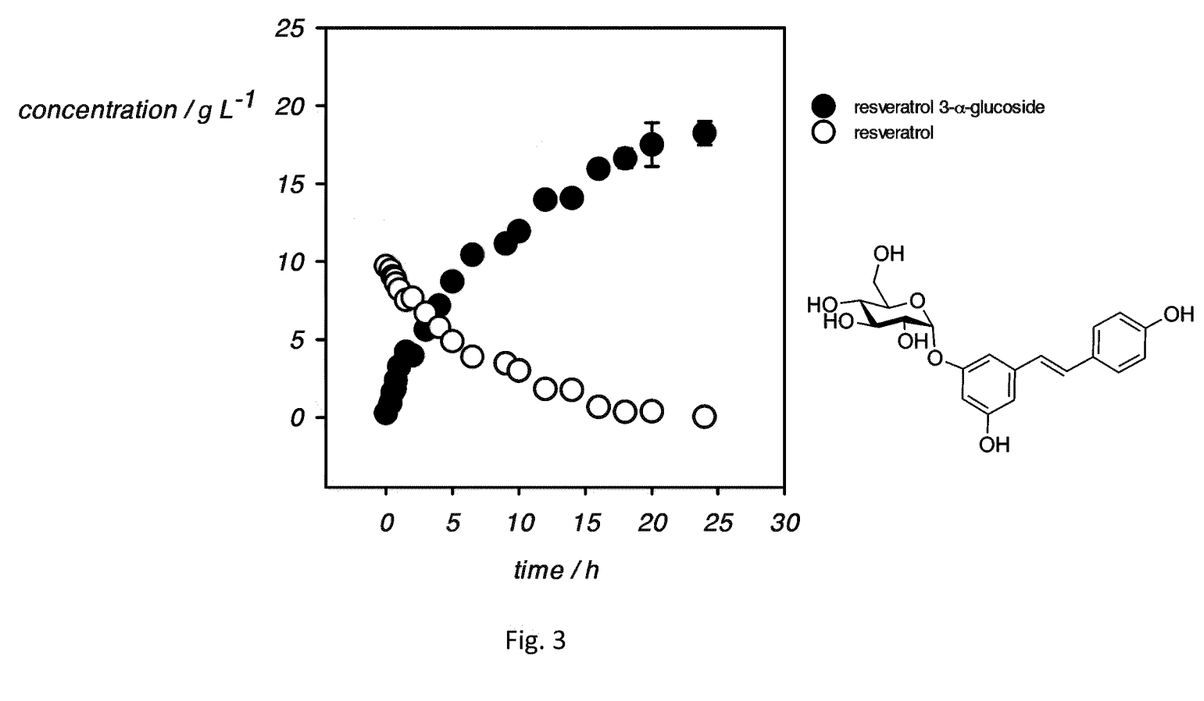
FIG. 3. Time course of resveratrol glycosylation by variant R134A (1 g·L$^{-1}$ enzyme, 10 g·L$^{-1}$ resveratrol and 1M sucrose at pH 6.5 and 55° C.)

The feasibility to use variant R134A as biocatalyst for the glycosylation of resveratrol in an aqueous system was then demonstrated by mixing the enzyme and 1 M sucrose with a saturated suspension of 10 g·L$^{-1}$ resveratrol. After 24 h incubation at 55° C., complete conversion of the acceptor was achieved (FIG. 3) and 17.1±0.6 g·L$^{-1}$ of resveratrol 3-alpha-glucoside was produced. The structure of the product was determined by NMR spectroscopy (see supplementary information) to confirm the strict regioselectivity of the enzyme. This production process not only is selective and efficient, but can also be easily implemented at larger, commercial scales.

REFERENCES

Aerts, D., Verhaeghe, T. F., Roman, B. I., Stevens, C. V., Desmet, T. and Soetaert, W. (2011b). Transglucosylation potential of six sucrose phosphorylases toward different classes of acceptors. Carbohydr. Res. 346:1860-1867.

Biagi, M. and Bertelli, A. A. E. (2015). Wine, alcohol and pills: What future for the French paradox? Life Sci.

Bornscheuer, U. T., Huisman, G. W., Kazlauskas, R. J., Lutz, S., Moore, J. C. and Robins, K. (2013). Engineering the third wave of biocatalysis. Nature. 485:185-194.

Breton, C., Fournel-Gigleux, S. and Palcic, M. M. (2012). Recent structures, evolution and mechanisms of glycosyltransferases. Curr. Opin. Struct. Biol. 1-10.

Bungaruang, L., Gutmann, A. and Nidetzky, B. (2013). Leloir Glycosyltransferases and Natural Product Glycosylation: Biocatalytic Synthesis of the C-Glucoside Nothofagin, a Major Antioxidant of Redbush Herbal Tea. Adv. Synth. Catal. 355:2757-2763.

Cerdobbel A, De Winter K, Desmet T, Soetaert W (2010) Sucrose phosphorylase as cross-linked enzyme aggregate: Improved thermal stability for industrial applications Biotechnol J, 5:1-6.

Cerdobbel, A., De Winter, K., Aerts, D., Kuipers, R., Joosten, H. J., Soetaert, W. and Desmet, T. (2011). Protein Eng., Des. Sel. 24:829-834.

Chaloupkova, R., Sykorova, J., Prokop, Z., Jesenska, A., Monincova, M., Pavlova, M., Tsuda, M., Nagata, Y. and Damborsky, J. (2003). Modification of Activity and Specificity of Haloalkane Dehalogenase from *Sphingomonas paucimobilis* UT26 by Engineering of Its Entrance Tunnel. J. Biol. Chem. 278:52622-52628.

de Roode, B. M., Franssen, M. C. R., van der Padt, A. and Boom, R. M. (2003). Perspectives for the Industrial Enzymatic Production of Glycosides. Biotechnol. Prog. 19:1391-1402.

De Winter, K., Desmet, T., Devlamynck, T., Van Renterghem, L., Verhaeghe, T., Pelantová, H., Křen, V. and Soetaert, W. (2014). Biphasic Catalysis with Disaccharide Phosphorylases: Chemoenzymatic Synthesis of α-d-Glucosides Using Sucrose Phosphorylase. Org. Process Res. Dev. 18:781-787.

De Winter, K., Verlinden, K., Křen, V., Weignerová, L., Soetaert, W. and Desmet, T. (2013). Green Chem. 15:1949-1955.

Desmet, T. and Soetaert, W. (2012). Process Biochemistry. Process Biochem. 47:11-17.

Desmet, T., Soetaert, W., Bojarová, P., Křen, V., Dijkhuizen, L., Eastwick-Field, V. and Schiller, A. (2012). Enzymatic Glycosylation of Small Molecules: Challenging Substrates Require Tailored Catalysts. Chem. Eur. J. 18:10786-10801.

Espín, J. C., Garcia-Conesa, M. T. and Tomas-Barberán, F. A. (2007). Nutraceuticals: Facts and fiction. Phytochemistry. 68:2986-3008.

Frémont (2000). Biological Effects of Resveratrol. Life Sci. 66:663-673.

Gantt, R. W., Peltier-Pain, P., Cournoyer, W. J. and Thorson, J. S. (2011). Using simple donors to drive the equilibria of glycosyltransferase-catalyzed reactions. Nat. Chem. Biol. 7:685-691.

Goedl, C., Sawangwan, T., Mueller, M., Schwarz, A. and Nidetzky, B. (2008). A High-Yielding Biocatalytic Process for the Production of 2-O-(α-D-glucopyranosyl)-sn-glycerol, a Natural Osmolyte and Useful Moisturizing Ingredient. Angew. Chem. Int. Ed. 47:10086-10089.

Gora, A., Brezovsky, J. and Damborsky, J. (2013). Gates of Enzymes. Chem. Rev. 113:5871-5923.

Kingsley, L. J. and Lill, M. A. (2015). Substrate tunnels in enzymes: Structure-function relationships and computational methodology. Proteins: Struct., Funct., Bioinf. 83:599-611.

Kitao, S., Ariga, T., Matsuda, T. and Sekine, H. (1993). The Syntheses of Catechin-glucosides by Transglycosylation with Leuconostoc mesenteroidesSucrose Phosphorylase. Biosci., Biotechnol., Biochem. 57:2010-2015.

Lairson, L. L., Henrissat, B., Davies, G. J. and Withers, S. G. (2008). Glycosyltransferases: Structures, Functions, and Mechanisms. Annu. Rev. Biochem. 77:521-555.

Maldonado O S, Lucas R, Comelles F, González M J, Parra J L, Medinac I, Morales J C (2011). Synthesis and characterization of phenolic antioxidants with surfactant properties: glucosyl- and glucuronosyl alkyl gallates. Tetrahedron 67: 7268-7279.

Mirza, O., Skov, L. K., Sprogoe, D., van den Broek, L. A. M., Beldman, G., Kastrup, J. S. and Gajhede, M. (2006). Structural Rearrangements of Sucrose Phosphorylase from *Bifidobacterium adolescentis* during Sucrose Conversion. J. Biol. Chem. 281:35576-35584.

Monsan, P., Remaud-Siméon, M. and André, I. (2010). Transglucosidases as efficient tools for oligosaccharide and glucoconjugate synthesis. Curr. Opin. Microbiol. 13:293-300.

Nestl, B. M. and Hauer, B. (2014). Engineering of Flexible Loops in Enzymes. ACS Catal. 4:3201-3211.

Novelle, M. G., Wahl, D., Diéguez, C., Bernier, M. and de Cabo, R. (2015). Resveratrol supplementation: Where are we now and where should we go? Ageing Res. Rev. 21:1-15.

Ozaki, S.-I., Imai, H., Iwakiri, T., Sato, T., Shimoda, K., Nakayama, T. and Hamada, H. (2011). Regioselective glucosidation of trans-resveratrol in Escherichia coli expressing glucosyltransferase from Phytolacca americana. Biotechnol. Lett. 34:475-481.

Palcic, M. M. (2011). Glycosyltransferases as biocatalysts. Curr. Opin. Chem. Biol. 1-8.

Park, E.-J. and Pezzuto, J. M. (2015). The pharmacology of resveratrol in animals and humans. Biochim. Biophys. Acta, Mol. Basis Dis. 1852:1071-1113.

Puchart, V. (2015). Glycoside phosphorylases: Structure, catalytic properties and biotechnological potential. Biotechnol. Adv. 1-16.

Quideau, S., Deffieux, D., Douat-Casassus, C. and Pouységu, L. (2011). Plant Polyphenols: Chemical Properties, Biological Activities, and Synthesis. Angew. Chem. Int. Ed. 50:586-621.

Sprogøe, D., van den Broek, L. A. M., Mirza, O., Kastrup, J. S., Voragen, A. G. J., Gajhede, M. and Skov, L. K. (2004). Crystal Structure of Sucrose Phosphorylase from Bifidobacterium adolescentis†. Biochemistry. 43:1156-1162.

Thuan, N. H. and Sohng, J. K. (2013). Recent biotechnological progress in enzymatic synthesis of glycosides. J. Ind. Microbiol. Biotechnol. 40:1329-1356.

Torres, P., Poveda, A., Jimenez-Barbero, J., Parra, J. L., Comelles, F., Ballesteros, A. O. and Plou, F. J. (2011). Enzymatic Synthesis of a-Glucosides of Resveratrol with Surfactant Activity. Adv. Synth. Catal. 353:1077-1086.

Verhaeghe, T., Aerts, D., Diricks, M., Soetaert, W. and Desmet, T. (2014). The quest for a thermostable sucrose phosphorylase reveals sucrose 6'-phosphate phosphorylase as a novel specificity. Appl. Microbiol. Biotechnol. 98:7027-7037.

The invention claimed is:

1. An in vitro method to glycosylate a polyphenol comprising:
    contacting in vitro a sucrose phosphorylase comprising the amino acid sequence of SEQ ID NO:1, SEQ ID NO:2, SEQ ID NO:3, SEQ ID NO:4 or SEQ ID NO:5 with sucrose or alpha-glucose-1-phosphate, and, a polyphenol, and
    glycosylating said polyphenol.

2. The in vitro method according to claim 1 wherein said polyphenol is a stilbenoid.

3. The in vitro method according to claim 2 wherein said stilbenoid is resveratrol.

4. The in vitro method according to claim 1 wherein said polyphenol is a flavonoid.

5. The in vitro method according to claim 4 wherein said flavonoid is apigenine, hesperetin, quercetin or epicatechin.

6. The in vitro method according to claim 1 wherein said polyphenol is a phenoxyphenol.

7. An in vitro method to glycosylate a polyphenol comprising:
    contacting in vitro a sucrose phoshorylase with sucrose or alpha-glucose-1 phosphate, and, a polyphenol, and,
    glycosylating said polyphenol, wherein said sucrose phoshorylase is a fragment of SEQ ID NO:1, SEQ ID NO:2, SEQ ID NO:3, SEQ ID NO:4 or SEQ ID NO:5 that has at least 90% sequence identity with SEQ ID NO:1, SEQ ID NO:2, SEQ ID NO:3, SEQ ID NO:4 or SEQ ID NO:5 and wherein said fragment comprises, in addition to having the amino acid A, V, T or G at position 134 of SEQ ID NO:1, SEQ ID NO:2, SEQ ID NO:3, or SEQ ID NO:4, respectively, or having a deletion at position 134 as shown by SEQ ID NO:5, at least the following 16 catalytic amino acids of SEQ ID NO:6: D49, F52, H87, F157, Q165, R195, D197, A198, Y201, E238, H240, H295, D296, D342, Q345 and R399, and
    wherein the fragment has an activity of glycosylation of polyphenols which is improved in comparison to the activity of the native sucrose phosphorylase of *Thermoanaerobacterium thermosaccharolyticum*.

8. A variant of the thermostable sucrose phosphorylase derived from the microorganism *Thermoanaerobacterium thermosaccharolyticum* comprising SEQ ID NO:1, SEQ ID NO:2, SEQ ID NO:3, SEQ ID NO:4 or SEQ ID NO:5, or, comprising a fragment of SEQ ID NO:1, SEQ ID NO:2, SEQ ID NO:3, SEQ ID NO:4 or SEQ ID NO:5 that has at least 90% sequence identity with SEQ ID NO:1, SEQ ID NO:2, SEQ ID NO:3, SEQ ID NO:4 or SEQ ID NO:5 and wherein said fragment comprises, in addition to having the amino acid A, V, T or G at position 134 of SEQ ID NO:1, SEQ ID NO:2, SEQ ID NO:3, or SEQ ID NO:4 respectively, or having a deletion at position 134 as shown by SEQ ID NO:5, at least the following 16 catalytic amino acids of SEQ ID NO:6: D49, F52, H87, F157, Q165, R195, D197, A198, Y201, E238, H240, H295, D296, D342, Q345 and R399, and
    wherein the fragment has an activity of glycosylation of polyphenols which is improved in comparison to the activity of the native sucrose phosphorylase of *Thermoanaerobacterium thermosaccharolyticum*.

* * * * *